(12) United States Patent
Almarsson et al.

(10) Patent No.: US 6,297,231 B1
(45) Date of Patent: *Oct. 2, 2001

(54) STABILIZED CARBAPENEM ANTIBIOTIC COMPOSITIONS AND METHOD OF MAKING

(75) Inventors: Orn Almarsson, Lansdale; Michael J. Kaufman, New Hope; John D. Stong, Collegeville, all of PA (US); John M. Williams, Belle Meade, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/284,321
(22) PCT Filed: Oct. 24, 1997
(86) PCT No.: PCT/US97/19336
  § 371 Date: Apr. 6, 1999
  § 102(e) Date: Apr. 6, 1999
(87) PCT Pub. No.: WO98/18800
  PCT Pub. Date: May 7, 1998

Related U.S. Application Data
(60) Provisional application No. 60/029,520, filed on Oct. 28, 1996.

(51) Int. Cl.$^7$ .................... C07D 477/20; A61K 31/407; A61P 31/04
(52) U.S. Cl. ..................... 514/210.13; 540/350
(58) Field of Search ................ 540/350; 514/210.13

(56) References Cited

U.S. PATENT DOCUMENTS 4,943,569  7/1990  Sunagawa ............... 514/210

FOREIGN PATENT DOCUMENTS 0 007 614   2/1980  (EP).
0 072 014   2/1983  (EP).
WO 94/14811  7/1994  (WO).

OTHER PUBLICATIONS

Y. Takeuchi et al., *Chem. Pharm.. Bull.*, 43(4), pp. 689–692 (1995).
S. H. Kim et al., *Res. Com.. Mol. Path. & Pharm.*, 90(3), pp. 347–362 (1995).
K. Inque et al., *Antimicro. Agts.*, & *Chemo.*, 39(10), pp. 2331–2336 (1995).
H–W. Lee, et al., *J. Antibiotics*, 48(9), pp. 1046–1048 (1995).
N.Ohtake et al., *J. Antibiotics*, 50(7); pp. 598–613 (1997).
C–H Oh et al., *J. Antibiotics*, 47(1); pp. 126–128 (1994).
Y. Iso et al., *J. Antibiotics*, 49(2); pp. 199–209 (1996).

Primary Examiner—Mark L. Berch
(74) Attorney, Agent, or Firm—Sylvia A. Ayler; Mark R. Daniel

(57) ABSTRACT

The present invention relates to a novel stabilized form of carbapenem antibiotics of formula II:

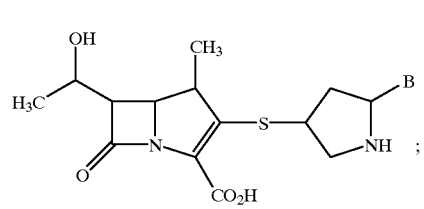

compositions and methods thereof wherein the antibiotics and compositions are stabilized degradation and dimer formation. The compounds can be used in the treatment of infectious diseases, including gram positive and negative, aerobic and anaerobic bacteria. The compounds provide good stability against beta-lactamases, and a favorable duration of action.

The compounds of this invention are represented structural formula I:

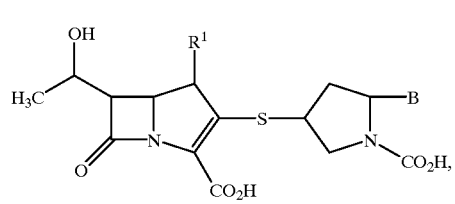

or a pharmaceutically acceptable or hydrate thereof.

23 Claims, 1 Drawing Sheet

STABILIZED CARBAPENEM ANTIBIOTIC COMPOSITIONS AND METHOD OF MAKING

This application claims the benefit of U.S. Provisional Application No. 60/029,520, filed Oct. 28, 1996.

BACKGROUND OF THE INVENTION

The present invention relates to a novel stabilized form of carbapenem antibiotics, compositions and methods thereof. The compounds can be used in the treatment of infectious diseases, including gram positive and negative, aerobic and anaerobic bacteria. The compounds provide good stability against beta-lactamases, and a favorable duration of action.

SUMMARY OF THE INVENTION

Figure 1:
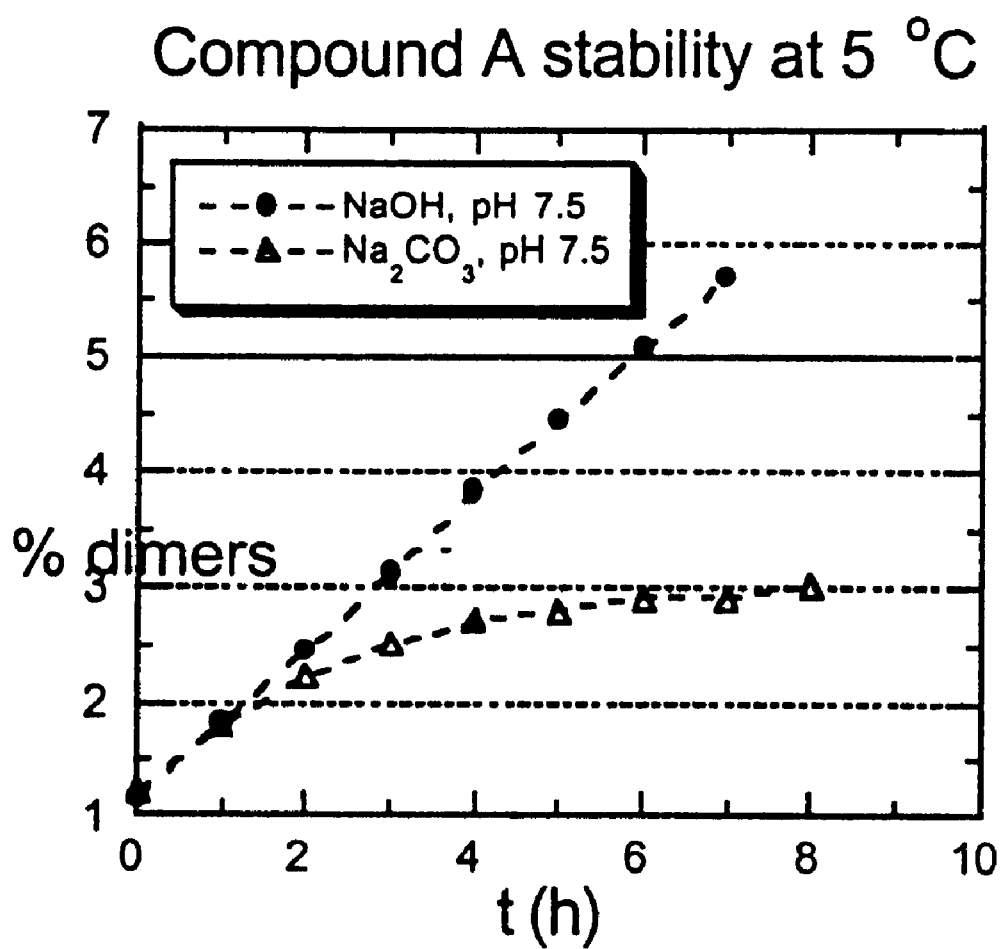
FIG. 1 illustrates the stabilization of carbapenem, Compound A at 5° C. A plot of % dimers versus time for Compound A in the presence of sodium carbonate and sodium hydroxide is provided. The plot of % dimers formed versus time in the presence of sodium carbonate exhibits about 5% dimer formation after about 8 hours at a pH of 7.5.

The present invention relates to a novel stabilized compound of formula I:

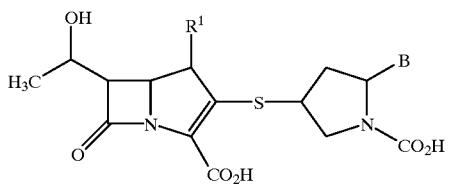

or a pharmaceutically acceptable salt, prodrug or hydrate thereof, wherein:

B is selected from a group consisting of H, CN,

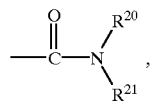

substituted or unsubstituted, straight or branch chain, bivalent $C_{1-6}$ alkyl, $C_{2-6}$ alkenyl, $C_{3-6}$ cycloalkyl or $C_{1-6}$ alkyl-X—$C_{1-6}$ alkyl wherein X is O, S, NH, or N($C_{1-6}$ alkyl), wherein said alkyl, alkenyl and alkenyl is optionally substituted with 1 to 3 groups selected from the group consisting of

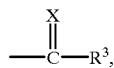

or $R^2$,

X is selected from the group consisting of O or NH, $R^3$ is selected from the group consisting of amino or heterocyclic amine group, each of which can be unsubstituted or substituted with

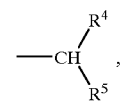

unsubstituted or substituted heterocyclic group, $C_{1-6}$ alkyl, aryl, heteroaryl, hydroxy($C_{1-6}$)alkyl, carbamoyloxy($C_{1-6}$)alkyl, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

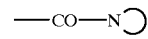

and

wherein

is an unsubstituted or substituted 3 to 6 membered heterocyclic ring which can contain additional hetero atoms, with the proviso that $R^4$ and $R^5$ cannot be hydrogen at the same time, $R^2$ is selected from the group consisting of hydroxy($C_{1-6}$)alkyl, carbamoyloxy, OH, $NR^6SO_2R^6$, $N(R^6)_2$, $R^6$ is selected from the group consisting of hydrogen or C1–6 alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl, pyridyl or $R^{20}$ and $R^{21}$ are taken together to represent an alkylene chain or alkylene chain via an oxygen atom, a sulfur atom or a (C2–C3) alkyl-substituted nitrogen atom to form, together with the adjacent nitrogen atom a substituted or unsubstituted 3 to 7 membered cyclic amino group which may contain double bond(s) in its ring, a substituted or unsubstituted guanidyl group of the formula

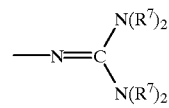

$R^7$ is selected from the group consisting of hydrogen, $C_{1-6}$ alkyl, a protected or unprotected OH group, a $C_{1-6}$ alkoxy, an unsubstituted or (C1–3)alkyl-substituted hydrazino group or a group of the formula —$NHOR^8$ wherein R8 is a hydrogen atom, a protecting group for a hydroxyl group or a $C_{1-6}$ alkyl, R1 is selected from the group consisting of H or $C_{1-6}$ alkyl.

The compounds are distinctly more stable than carbapenem compounds such as meropenem with respect to intermolecular dimerization degradation (See Takeuchi et al., *Chem. Pharm. Bull.* 43(4), 689–692 (1995), regarding degradates of meropenem) See also Kim, S H et al., *Res. Com. Mol. Path. & Pharm.*, 90(3), 347–362 (1995), regarding DA-1131; Inoue K. et al., *Antimicro. Agts & Chemo.*, 39(10), 2331–2336 (1995), regarding BO-2727 and Lee H. W. et al., *J. Antibiotics*, 48(9), 1046–1048 (1995). The compounds can be used in the treatment of infectious diseases, including gram positive and negative, aerobic and anaerobic bacteria. The compounds provide good stability against beta-lactamases, and a favorable duration of action. Compound I is a carbapenem antibiotic that is particularly useful for intravenous and intramuscular administration.

DESCRIPTION OF THE DRAWINGS

FIG. 1 shows the percentage of dimer formation of Compound A in the presence of sodium carbonate (triangles) and in the absence of carbonate, at pH 7.5 in solution over time (hours), prior to lyophilization.

DETAILED DESCRIPTION OF THE INVENTION

As used herein, the term "stabilized form" refers to compounds which have a carbamate group formed at the pyrrolidine nitrogen atom, as shown in compounds of formula I. This carbamate is obtainable by combining a compound of formula II or a salt, prodrug or hydrate thereof with a carbon dioxide source, such as sodium carbonate or sodium bicarbonate. Examples are shown as formula I and I-a through I-c.

The term "pro-drug" refers to compounds with a removable group attached to the hydroxyl of the hydroxyethyl side chain (position 6 of the carbapenem nucleus), the carboxylic acid at position 3 of the carbapenem nucleus or the meta-carboxylic acid group on the phenyl ring of the side chain. Groups which are useful in forming pro-drugs should be apparent to the medicinal chemist from the teachings herein. Examples include allyl, acetyl, benzyloxycarbonyl, methoxymethyl, t-butoxycarbonyl, trimethylsilyl and the like.

The term "hydrate" is used in the conventional sense to include the compounds of formula I and II in physical association with water.

In this application "alkyl" means straight, cyclic or branched alkyl with the indicated number of carbon atoms. "Halo" means chloro, bromo, fluoro or iodo. Aryl refers to aromatic rings e.g., phenyl, substituted phenyl and like groups as well as rings which are fused, e.g., naphthyl and the like. The preferred aryl groups are phenyl and naphthyl. The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like. Carbamoyl (C1-6)alkyl may include, for example carbamoylmethyl, carbamoylethyl, carbamoylpropyl, carbamoylbutyl, 1-(carbamoylmethyl)ethyl, 1-carbamoyl-1-methylethyl, 1,1-dimethyl-2-carbamoylethyl, carbamoylpentyl, carbamoylhexyl and the like, preferably a carbamoyl($C_{1-4}$)alkyl. The term alkylene may include, for example methylene, ethylene, trimethylene, tetramethylene, pentamethylene, hexamethylene, methylethylene, ethylethylene, propylene and the like, preferably $C_{1-4}$ alkylene.

In the definition of $R^4$ and $R^5$,

means a 3 to 6 membered heterocyclic group which may contain additional heteroatoms, preferably nitrogen. Examples are substituted or unsubstituted aziridinyl, azetidinyl, pyrrolidinyl, piperidinyl or piperazinyl, in which the preferable substituent may be carbamoyl, $C_{1-6}$ alkyl, hydroxy $C_{1-6}$ alkyl, cyano $C_{1-6}$ alkyl, amino $C_{1-6}$ alkyl, carbamoyloxy $C_{1-6}$ alkyl or amino.

Substituted or unsubstituted heterocyclic amine preferably means a N-containing heterocyclic group, particularly aziridinyl, azetidinyl, pyrrolidinyl, piperidinyl or piperazinyl, which the substituent may be carbamoyl, $C_{1-6}$ alkyl, hydroxy $C_{1-6}$ alkyl, cyano $C_{1-6}$ alkyl, amino $C_{1-6}$ alkyl, carbamoyloxy $C_{1-6}$ alkyl, ureido $C_{1-6}$ alkyl, carbamoyl $C_{1-6}$ alkyl or mono or di-$C_{1-6}$ alkyl carbamoyl$C_{1-6}$ alkyl.

Carboxy-protecting groups can be a group which can form esterified carboxy such as $C_{1-6}$ alkyl ester, which include methyl ester, ethyl ester, propyl ester and the like, $C_{1-6}$ alkanoyloxy $C_{1-6}$ alkyl ester such as acetoxymethyl ester, propionyloxymethyl ester, butyryloxymethyl ester, valeryloxymethyl ester, pivaloyloxymethyl ester and the like.

Imino-protecting groups can be acyl group such as aliphatic acyl substituted with aromatic or heterocyclic group derived from carboxylic acid, carbonic acid, sulfonic acid or carbamic acid, or carbamoyl, aliphatic acyl, aromatic acyl or heterocyclic acyl. Suitable aliphatic acyl groups include formyl, acetyl, propionyl, butyryl and the like.

One subset of compounds of the invention relates to compounds of formula I wherein B is selected from a group consisting of

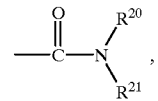

substituted or unsubstituted, straight or branch chain, $C_{1-6}$ alkyl, $C_{2-6}$ alkenyl, $C_{3-6}$ cycloalkyl or $C_{1-6}$ alkyl-X—$C_{1-6}$ alkyl wherein X is O, S, or NH, wherein said alkyl, and alkenyl is optionally substituted with 1 to 3 groups selected from the group consisting of

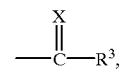

or $R^2$ and X is O. Within this subset, all other variables are as originally defined.

Another subset of compounds of the invention relates to compounds of formula I wherein $R^3$ is

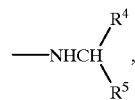

wherein $R^4$ and $R^5$ independently are selected from the group consisting of H, hydroxy($C_{1-4}$)alkyl, CN, carbamoyl ($C_{1-4}$)alkyl, cyano($C_{1-4}$)alkyl, ureido($C_{1-4}$)alkyl, or piperazinyl optionally mono-substituted with carbamoyl, $C_{1-6}$ alkyl, hydroxy($C_{1-4}$)alkyl, CN, carbamoyl($C_{1-4}$)alkyl, cyano($C_{1-4}$)

alkyl, ureido($C_{1-4}$)alkyl, amino ($C_{1-4}$)alkyl, carbamoyloxy ($C_{1-4}$)alkyl or mono- or di-($C_{1-4}$)alkyl alkylcarbamoyl($C_{1-4}$) alkyl, with the proviso that $R^4$ and $R^5$ cannot be hydrogen at the same time, and $R^2$ is selected from the group consisting of hydroxy($C_{1-6}$)alkyl, carbamoyloxy, OH, and $NR^6SO_2R^6$, $N(R^6)_2$. Within this subset, all other variables are as originally defined.

A preferred subset of compounds of the invention relates to compounds of formula I wherein:

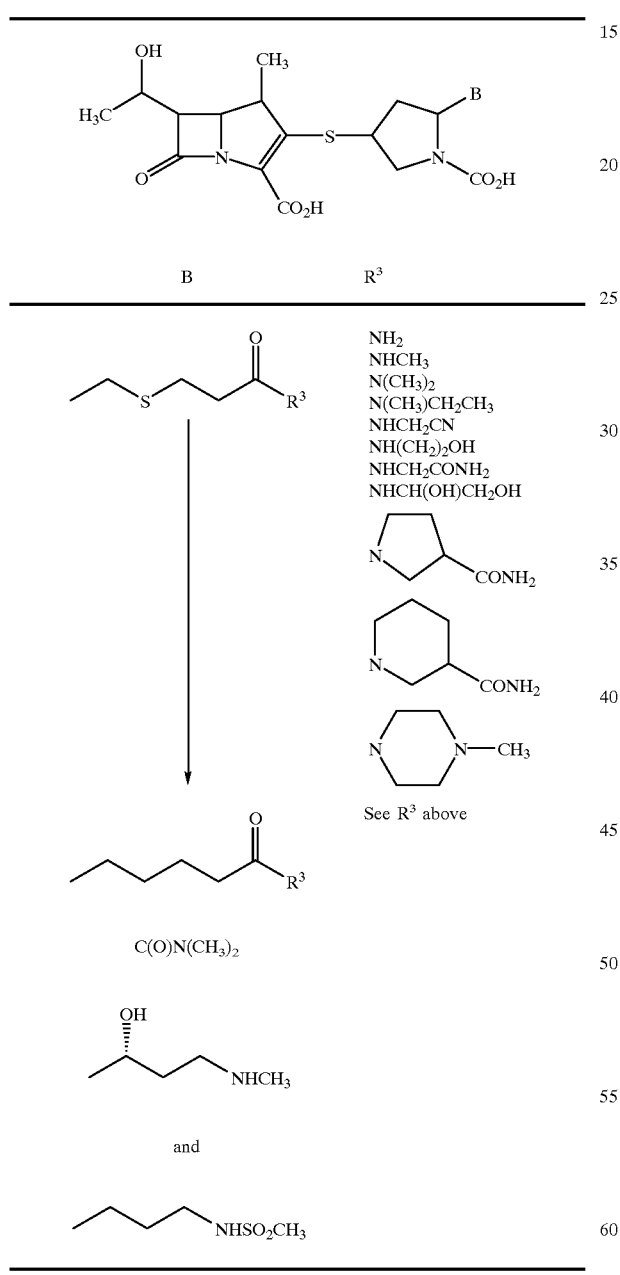

Another aspect of the invention relates to pharmaceutical compositions which contain the carbapenem antibiotic compound I:

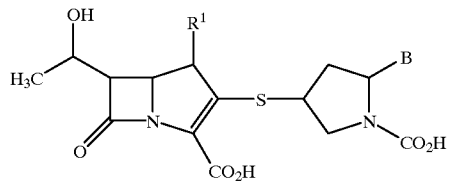

or a pharmaceutically acceptable salt, prodrug or hydrate thereof, in combination with a pharmaceutically acceptable carrier, wherein:

B is selected from a group consisting of $C(O)N(R^6)_2$, H, OH, CN, substituted or unsubstituted, straight or branch chain, $C_{1-6}$ alkyl, $C_{2-6}$ alkenyl, $C_{3-6}$ cycloalkyl or $C_{1-6}$ alkyl-X—$C_{1-6}$ alkyl wherein X is O, S, NH, or N($C_{1-6}$ alkyl), wherein said alkyl, and alkenyl is optionally substituted with 1 to 3 groups selected from the group consisting of

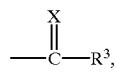

or $R^2$,

X is selected from the group consisting of O or NH, $R^3$ is selected from the group consisting of amino or heterocyclic amine group, each of which can be unsubstituted or substituted with

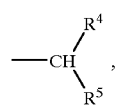

unsubstituted or substituted heterocyclic group, C1–6 alkyl, aryl, heteroaryl, hydroxy($C_{1-6}$)alkyl, carbamoyloxy($C_{1-6}$)alkyl, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

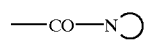

and

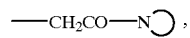

wherein

is an unsubstituted or substituted 3 to 6 membered heterocyclic ring which can contain additional hetero atoms, with the proviso that $R^4$ and $R^5$ cannot be hydrogen at the same time, $R^2$ is selected from the group consisting of hydroxy($C_{1-6}$) alkyl, carbamoyloxy, OH, and $NR^6SO_2R^6$, $N(R^6)_2$, $R^6$ is selected from the group consisting of hydrogen or C1–6 alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl, pyridyl or $R^{20}$ and $R^{21}$ are taken together to represent an alkylene chain or alkylene chain an oxygen atom, a sulfur atom or a (C2–C3) alkyl-substituted nitrogen atom to form, together with the adjacent nitrogen atom a substituted or unsubstituted 3 to 7 membered cyclic amino group which may contain double bond(s) in its ring, a substituted or unsubstituted guanidyl group of the formula

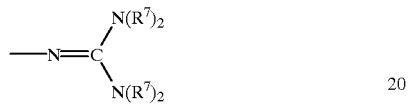

$R^7$ is selected from the group consisting of hydrogen, $C_{1-6}$ alkyl, a protected or unprotected OH group, a $C_{1-6}$ alkoxy, an unsubstituted or (C1–3)alkyl-substituted hydrazino group or a group of the formula —$NHOR^8$ wherein R8 is a hydrogen atom, a protecting group for a hydroxyl group or a $C_{1-6}$ alkyl, R1 is selected from the group consisting of H or $C_{1-6}$ alkyl.

Still another aspect of the present invention relates to a compound of structural formula I which is produced by combining a compound of formula II:

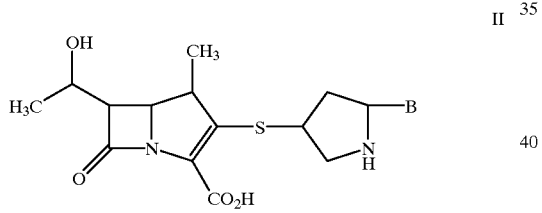

II or a pharmaceutically acceptable salt, prodrug or hydrate thereof with a carbon dioxide source, wherein:

B is selected from a group consisting of H, CN,

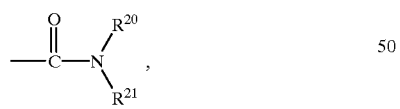

substituted or unsubstituted, straight or branch chain, $C_{1-6}$ alkyl, $C_{2-6}$ alkenyl, $C_{3-6}$ cycloalkyl or $C_{1-6}$ alkyl-X-$C_{1-6}$ alkyl wherein X is O, S, NH, or N($C_{1-6}$ alkyl), wherein said alkyl, alkenyl and alkenyl is optionally substituted with 1 to 3 groups selected from the group consisting of

or $R^2$,

X is selected from the group consisting of O or NH, $R^3$ is selected from the group consisting of amino or heterocyclic amine group, each of which can be unsubstituted or substituted with

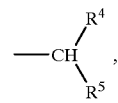

unsubstituted or substituted heterocyclic group, C1–6 alkyl, aryl, heteroaryl, hydroxy($C_{1-6}$)alkyl, carbamoyloxy($C_{1-6}$)alkyl, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

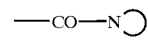

and

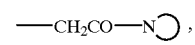

wherein

is an unsubstituted or substituted 3 to 6 membered heterocyclic ring which can contain additional hetero atoms, with the proviso that $R^4$ and $R^5$ cannot be hydrogen at the same time, $R^2$ is selected from the group consisting of hydroxy($C_{1-6}$) alkyl, carbamoyloxy, OH, $NR^6SO_2R^6$, $N(R^6)_2$, $R^6$ is selected from the group consisting of hydrogen or C1–6 alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl, pyridyl or $R^{20}$ and $R^{21}$ are taken together to represent an alkylene chain or alkylene chain an oxygen atom, a sulfur atom or a (C2–C3) alkyl-substituted nitrogen atom to form, together with the adjacent nitrogen atom a substituted or unsubstituted 3 to 7 membered cyclic amino group which may contain double bond(s) in its ring, a substituted or unsubstituted guanidyl group of the formula

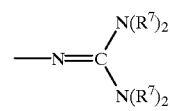

$R^7$ is selected from the group consisting of hydrogen, $C_{1-6}$ alkyl, a protected or unprotected OH group, a $C_{1-6}$ alkoxy, an unsubstituted or (C1–3)alkyl-substituted hydrazino group or a group of the formula —$NHOR^8$ wherein R8 is a hydrogen atom, a protecting group for a hydroxyl group or a $C_{1-6}$ alkyl, R1 is selected from the group consisting of H or $C_{1-6}$ alkyl.

Yet another aspect of this invention relates to a compound wherein the carbon dioxide source is selected from carbon dioxide, potassium, magnesium, calcium and sodium carbonates/bicarbonates.

A still further aspect of the invention relates to a method of stabilizing a carbapenem compound of the formula II:

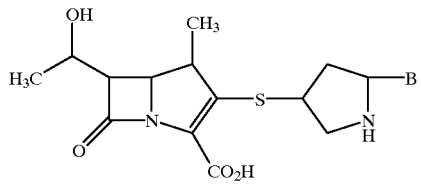

II or a pharmaceutically acceptable salt, prodrug or hydrate thereof, wherein:

B is selected from a group consisting of H, CN,

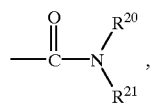

substituted or unsubstituted, straight or branch chain, $C_{1-6}$ alkyl, $C_{2-6}$ alkenyl, $C_{3-6}$ cycloalkyl or $C_{1-6}$ alkyl-X-$C_{1-6}$ alkyl wherein X is O, S, NH, or N($C_{1-6}$ alkyl), wherein said alkyl, and alkenyl is optionally substituted with 1 to 3 groups selected from the group consisting of

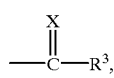

or $R^2$,

X is selected from the group consisting of O or NH, $R^3$ is selected from the group consisting of amino or heterocyclic amine group, each of which can be unsubstituted or substituted with

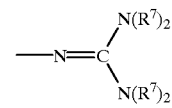

unsubstituted or substituted heterocyclic group, $C_{1-6}$ alkyl, aryl, heteroaryl, hydroxy($C_{1-6}$)alkyl, carbamoyloxy($C_{1-6}$)alkyl, said alkyl, aryl, heteroaryl optionally substituted with 1 to 3 groups selected from H, $COOR^6$, halo, $CF_3$, $C_{1-6}$ alkyl, OH and $N(R^6)_2$, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

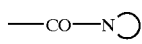

and

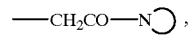

wherein

is an unsubstituted or substituted 3 to 6 membered heterocyclic ring which can contain additional hetero atoms, with the proviso that $R^4$ and $R^5$ cannot be hydrogen at the same time, $R^2$ is selected from the group consisting of hydroxy($C_{1-6}$) alkyl, carbamoyloxy, OH, $NR^6SO_2R^6$, $N(R^6)_2$, $R^6$ is selected from the group consisting of hydrogen or C1–6 alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl, pyridyl or $R^{20}$ and $R^{21}$ are taken together to represent an alkylene chain or alkylene chain an oxygen atom, a sulfur atom or a (C2–C3) alkyl-substituted nitrogen atom to form, together with the adjacent nitrogen atom a substituted or unsubstituted 3 to 7 membered cyclic amino group which may contain double bond(s) in its ring, a substituted or unsubstituted guanidyl group of the formula $$-N=C\begin{matrix}N(R^7)_2\\N(R^7)_2\end{matrix}$$

$R^7$ is selected from the group consisting of hydrogen, $C_{1-6}$ alkyl, a protected or unprotected OH group, a $C_{1-6}$ alkoxy, an unsubstituted or (C1–3)alkyl-substituted hydrazino group or a group of the formula —$NHOR^8$ wherein R8 is a hydrogen atom, a protecting group for a hydroxyl group or a $C_{1-6}$ alkyl, R1 is selected from the group consisting of H or $C_{1-6}$ alkyl; comprising dissolving a compound of formula II and a sufficient amount of a carbon dioxide source in a solvent to form a solution containing a compound of formula I:

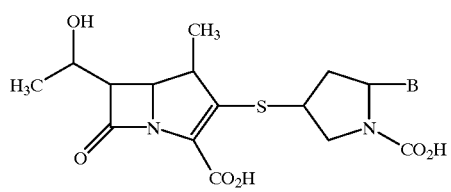

I or a pharmaceutically acceptable salt, prodrug or hydrate thereof, wherein B is described above. The method, wherein the carbon dioxide source is selected from the group consisting of carbon dioxide, potassium, magnesium, calcium and sodium carbonates/bicarbonates and the solvent is selected from the group consisting of water or saline.

Another aspect of the method relates to the solution wherein it is lyophilized to provide a composition containing a compound of formula I, or a salt, prodrug or hydrate thereof.

Yet another aspect of the invention relates to a pharmaceutical composition which is comprised of a compound represented by formula II:

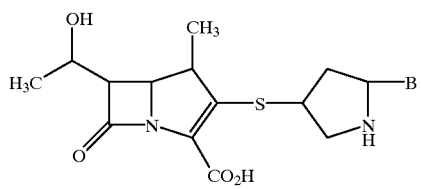

II or a pharmaceutically acceptable salt, stabilized form, prodrug or hydrate thereof, in combination with carbon dioxide source.

Compound I is a carbapenem antibiotic that is particularly useful for intravenous and intramuscular administration.

The pharmaceutical composition can be formulated with any pharmaceutically acceptable buffer which will provide a pH of about 6.0 to about 9.0 upon dissolution. For example, sodium bicarbonate is a preferred pharmaceutically acceptable buffer. Preferably the pH of the composition upon dissolution is about 6.2 to about 8.5.

The pharmaceutical composition of the present invention are generally formulated using a carbon dioxide source. Preferred sources of carbon dioxide are carbon dioxide (gas, liquid or solid), carbonates and bicarbonates such as potassium, magnesium, calcium and sodium carbonates/bicarbonates, and more preferably sodium carbonate and sodium bicarbonate, which can be incorporated into the formulation, such that an appropriate pH, e.g., about 6.2–8.5, is obtained upon dissolution.

Compounds of formula II can be synthesized in accordance with U.S. Pat. No. 4,943,569 issued to Sunagawa, M. on Jul. 24, 1990, the teachings of which are incorporated herein by reference. See also U.S. Pat. No. 4,888,344, incorporated herein by reference. Additional starting compounds are also taught in PCT WO 94/14811, incorporated herein, and can be synthesized by methods known in the art or in accordance with the non-limiting examples below.

Scheme 1 below depicts one method of preparing the instant compounds.

Scheme 1

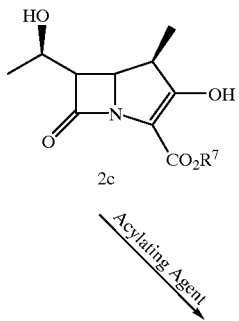

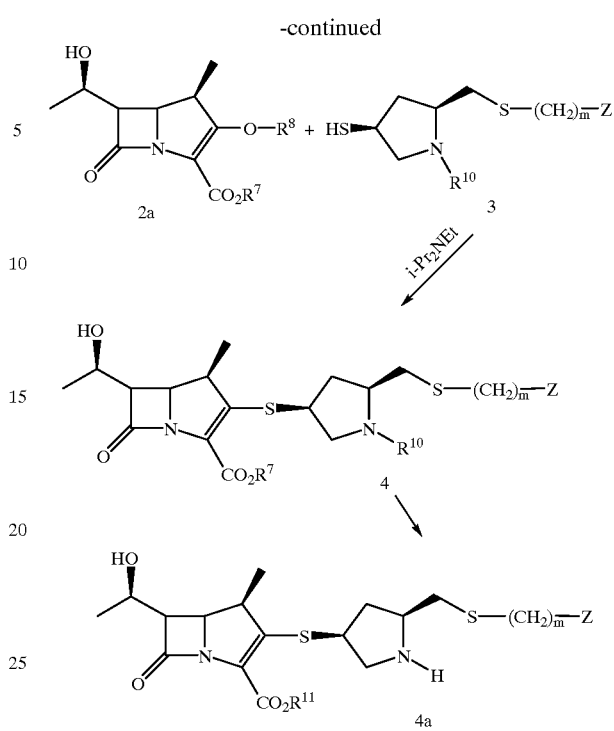

A carbapenem derivative of formula 2c or a reactive derivative at the oxo group thereof (2a) or a salt thereof is reacted with a mercaptopyrrolidine derivative of formula 3 or a salt thereof to prepare a compound of formula 4 or a salt thereof. The reactive derivative can be prepared by reacting the compound of formula 2c with an acylating agent $R^8$ which may include conventional ones such as organic sulfonic acid, organic phosphoric acid, or its reactive derivative such as acid halide or acid anhydride, for example benzenesulfonyl chloride, p-bromobenzene sulfonyl chloride, diphenyl phosphorochloridate, diethyl phosphorochloridate and the like. $R^7$ is a carboxy protecting group and $R^{10}$ is an imino protecting group.

The acylation is preferably carried out in the presence of a solvent and any conventional organic solvent such as acetone, dioxane acetonitrile, chloroform, dichloromethane, benzene, pyridine, ethyl acetate and the like, can be used, preferably benzene or acetonitrile. If the acylating agent is used in the form of a free acid or its salt the reaction is usually carried out in the presence of a condensing agent. Suitable condensing agents are N,N-diethylcarbodiimide, N,N-diisopropylcarbodiimide, and the like, imidazole compounds such as N,N-carbonyldiimidazole and the like, Keteneimine compounds such as pentamethyleneketene-N-cyclohexylamine and the like. Additionally, the acylation may be carried out in the presence of an inorganic or organic base such as hydroxides, carbonates, bicarbonates or alkanoates of an alkali metal such as lithium, sodium or potassium, etc., tri-$C_{1-6}$ alkylamines such as triethylamine, N,N-diisopropyl-N-ethylamine and the like, preferably N,N-diisopropyl-N-ethylamine.

The acylation reaction is generally carried out under cooling to warming, for example, at the temperature of −40° C. to 50° C., preferably at −20° C. to 20° C. The reaction time is generally from about 0.5 to 3 hours. In this reaction, 1 to 3 moles of the base and 1 to 3 moles of the acylating agent are used with respect to one mole of the compound of formula 2c.

The compound of formula 2a or salt thereof can subsequently be reacted with the compound of formula 3 or salts thereof to prepare the compound of formula 4 or salts thereof. In this reaction the compound of formula 2a can be used with or preferably without isolation. The reaction can be carried out in a reaction-inert solvent such as those described in the acylation reaction, preferably acetonitrile, or DMF. The reaction temperature can be varied within a substantially wide range.

The compounds of formula 4 or salts thereof are subjected to elimination reaction of the carboxy-protecting group $R^7$ as well as elimination of the imino-protecting group to prepare the compound Ia or salts thereof, wherein $R^{11}$ is hydrogen or anion. The removal of the carboxy-protecting and imino-protecting groups can be carried out by conventional methods known in the art such as hydrolysis, reduction and the like. If necessary, elimination of both carboxy-protecting and imino-protecting groups can be carried out in the same reaction vessel without isolation of the intermediate compound.

The process for making the mercaptopyrrolidine derivative of formula 3 is depicted in Scheme 2 below.

Scheme 2

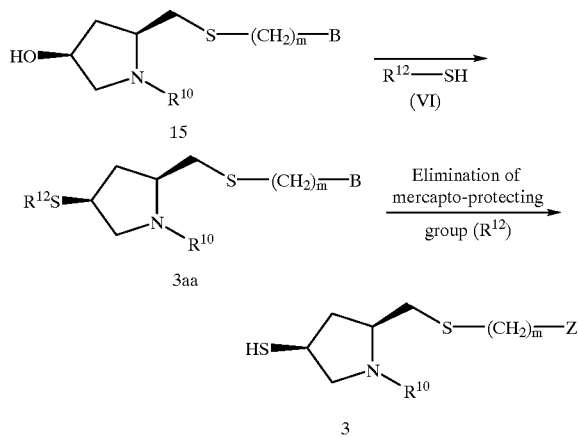

In the reaction above, $R^{12}$ is a mercapto-protecting group, m is an integer from 1 to 6 and R10 and B are described above. The mercapto-protecting group can be an acyl group as stated above in connection with the imino-protecting group, aryl $C_{1-6}$ alkyl such as mono or di- or tri-phenyl $C_{1-6}$ alkyl, for example benzyl, phenylethyl, benzhydryl, trityl and the like, preferably $C_{1-4}$ alkanoyl, aroyl and triphenyl $C_{1-4}$ alkyl.

The compound of formula V or a reactive derivative at the hydroxy group thereof or salts thereof can be reacted with the mercaptan derivative of formula VI or salts thereof to prepare a compound of formula 3aa or salts thereof. A suitable reactive derivative at the hydroxy group of the compound of formula 15 can be a halide such as chloride, bromide, iodide, etc., sulfonates such as methanesulfonate, benzenesulfonate, toluenesulfonate, etc. In the case where compound 15 is a methanesulfonate derivative, the reaction can be carried out, for example, by reacting one equivalent weight of the compound of formula VI with 1 to 2 equivalent weight, preferably 1.2 equivalent weight, of the methanesulfonate compound of formula V and 1 to 2 equivalent weight, preferably 1.2 equivalent weight, of an organic or inorganic base in a halogenated alkane solvent such as dichloromethane, at the temperature of −10° C. to 40° C., preferably −5° C. to 0° C., for 1 to 3 hours. The mercaptan derivative of formula VI may be aryl(lower)alkanethiol such as mono- or di- or triphenyl(lower)alkanethiol, for example, phenylmethanethiol, diphenylmethanethiol, triphenylmethanethiol, and the like, thioacetic-S-acid, thiobenzoic-S-acid, preferably thioacetic-S-acid or its potassium salt.

The mercapto-protecting group of the compound of formula 3aa or salts thereof is then eliminated to provide the compound of formula 3 or salts thereof. The elimination reaction is carried out by means of a conventional method and can be appropriately selected depending on the kind of mercapto-protecting group to be eliminated. For example, when the protecting group is aryl($C_1$–$C_6$)alkyl group, elimination can occur by treating with a silver compound such as silver nitrate or silver carbonate. The elimination reaction with silver is preferably carried out in the presence of an organic base such as pyridine, etc. The resulting silver salt of the compound of formula 3 can be converted into its alkali metal salt, if necessary, by treating with alkali metal halide such as sodium iodide, potassium iodide, etc.

The compounds of formula 4a, 2c, 2a, 3, 3aa, 4 and salts thereof can be isolated and purified employing means of a conventional manner, for example extraction, precipitation, fractional crystallization, recrystallization, column chromatography and the like.

Suitable salts of the compounds of formula 2c, 2a, 3, 4, and 4a, which are used as starting materials and reactants or obtained as reaction products, may be the same as those specifically exemplified in connection with the salts of the compound of formula I.

Examples of a compound of formula II are discussed below.

EXAMPLE 1

(1R,5S,6S)-[(2S,4S)-2-((carbamoylethyl)mercaptomethyl)pyrrolidin-4-yl]thio-6-[(R)-1-hydroxyethyl]-1-methylcarbapen-2-em-3-carboxylic Acid

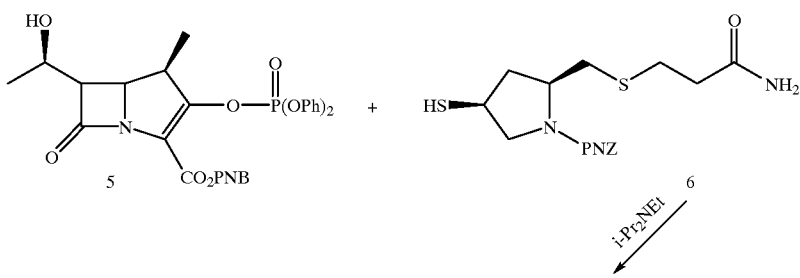

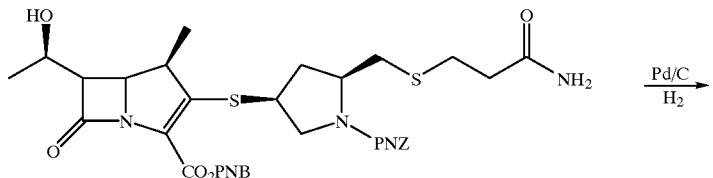
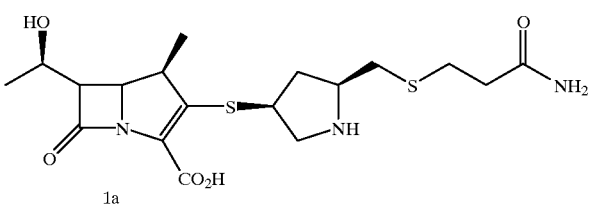
Treatment of enolphosphate (5) with freshly prepared thiol compound (6) affords 2-substituted carbapenem (7), which is deprotected by hydrogenolysis over 10% Pd—C in the presence of 3-morpholinopropanesulfonic acid (MOPS) buffer (0.1 M, pH=7.0) to provide (1a). 1(a) was purified by column chromatography on diaion HP-20.
1H NMR (D20) g 1.26 (3H, d, J=8 Hz), 1.33 (3H, d, J=8 Hz), 2.17~2.50 (4H, m), 2.65~2.95 (2H, m).
EXAMPLE 2
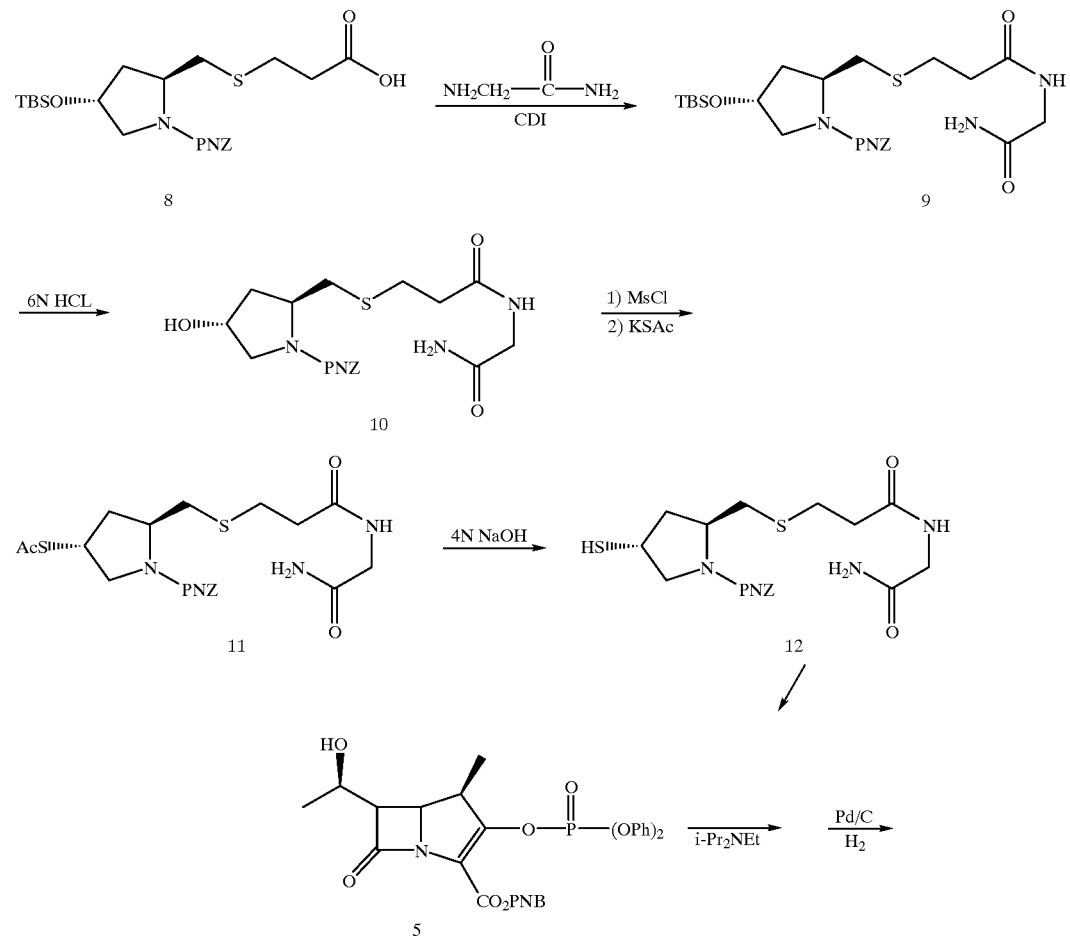

-continued

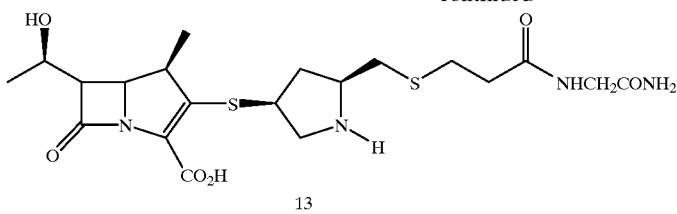

13

Substitution of compound 8 with glycinamide in acetonitrile affords carbamoylmethylcarbamoylalkylpyrrolidine compound 9. Desilylation of compound 9 carried out with 6N HCL in methanol to give hydroxymethylcarbamoylpyrrolidine compound 10. After mesylation of compound 10, the mesylated carbamoylpyrrolidine compound is converted into the acetylthiocarbamoylmethyl carbamoylpyrrolidine compound 11 with potassium thioacetate in DMF, whose acetylthio group is readily hydrolyzed with 4 N NaOH to give thiol compound 12. Compound 12 is reacted with compound 5 to give compound 13.

The compounds of formula II in lyophilized or non-lyophilized form, combined with the compound which produces carbon dioxide, such as sodium carbonate or sodium bicarbonate, is converted to a compound of formula I.

Generally compounds of formula I can be synthesized by combining a compound of formula II with the carbon dioxide source, and then dissolving the blend in an appropriate solvent.

In many instances it is preferred to dissolve the compound of formula II with the carbon dioxide producing compound, in an aqueous solvent, and then lyophilize the resulting composition, thus providing a mixture containing compounds of formula I.

Upon dissolution, the compound of formula I (I and I-a through II-c) converts into a compound of formula II (II, and II-a,) over time.

The compound of formula II can be powder blended with a carbon dioxide producing compound, such that the compound of formula I, or the salt, prodrug or hydrate thereof, is produced upon dissolution or reconstitution.

Alternatively, the compound of formula II and the carbon dioxide producing compound can be combined in solution to form compound I, after which the composition is lyophilized to provide a composition containing a compound of formula I, or a salt, prodrug or hydrate thereof.

The amount of carbonate or bicarbonate used in the process can be varied within wide limits. For example, the amount of sodium carbonate can be varied from as low as about 0.025 g of sodium carbonate/gram of drug to as high as about 0.25 g of sodium carbonate/gram of drug. Likewise, the amount of sodium bicarbonate in the formulation can be varied from as low as about 0.025 g/gram of drug, to as high as about 0.7 g/gram of drug. Other compounds can be included to adjust the pH of the composition upon dilution or reconstitution. Examples include potassium hydroxide, sodium hydroxide, N-methyl glucamine and the like.

One formulation that is of particular interest is comprised of about 3–6 parts by weight, and preferably about 4.5 parts by weight, of the compound of formula II, or the pharmaceutically acceptable salt, stabilized form, prodrug or hydrate thereof, and 1 part by weight of sodium bicarbonate. The pH which results upon dissolution of this formulation is approximately 6.5. Formulating the drug in this manner can extend the stability of the product in solution.

Another formulation that is of particular interest is comprised of about 4–10 parts by weight, and preferably about 6.7 parts by weight, of the compound of formula II, or the pharmaceutically acceptable salt, stabilized form, prodrug or hydrate thereof, and 1 part by weight sodium carbonate. The pH which results upon dissolution of this formulation is approximately 7.5. Formulating the drug in this manner can extend the stability of the product in solution.

As mentioned above, the compound of formula I or II can be used in lyophilized or non-lyophilized form. The lyophilized form is produced using standard lyophilization techniques.

Additional components can be included in the compositions of the present invention as well. Since the composition is preferably administered by injection, various diluents, buffers, preservatives, local anesthetics, tonicity controlling agents and other components can be included.

Representative examples of diluents include sterile water for injection, normal saline, dextrose solution 5% (D5W), lactated Ringer's solution and the like. Preferably the diluent is normal saline or sterile water for injection.

Representative examples of buffers include phosphate buffer, such as dihydrogen sodium phosphate, citrate buffer, such as sodium citrate, meglumine and tri(hydroxymethyl) aminomethane.

Representative examples of preservatives include butylhydroxyacetone (BHA), butylhydroxytoluene (BHT) and benzalkonium chloride.

Representative examples of local anesthetics include benzocaine, lidocaine, novacaine, pontocaine and the like.

Representative examples of tonicity modifying agents include sodium chloride, mannitol, dextrose, glucose, lactose and sucrose.

Representative examples of pharmaceutical excipients include water, mannitol, sorbitol, dextrose, lactose, glucose, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids.

When the compound of formula II is formulated in a pharmaceutical composition with a suitable amount of carbonate or bicarbonate, any or all of the species described herein can be contained in the formulation upon dilution or reconstitution. Compound II represents the non-stabilized form of the free acid. Thus, various salt forms of formula II, including II-a are included herein.

II-a

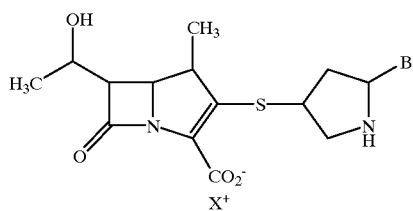

$X^+$

The specie $X^+$ represents a charge balancing cation, which is present in association with the compound as necessary to maintain overall charge neutrality. Typically the charged specie would be a pharmaceutically acceptable salt-forming ion, such as sodium, potassium, magnesium and the like. A divalent specie such as $Ca^{2+}$ can likewise be present, such as when two carboxylate anions are found in the compound, as in formula II-a, When the counterion includes a bis cationic specie, e.g., $Ca^{+2}$ an appropriate amount is typically present relative to the carbapenem moiety to provide overall charge neutrality. Thus, the half molar equivalent of $Ca^{+2}$ can be included with a monocarboxylate to maintain overall charge neutrality. All such embodiments are included in the present invention.

Numerous salt-forming ions are recited in Berge, S. M., et al. J. Pharm. Sci. 66(1): 1–16 (1977), the teachings of which are incorporated herein by reference.

A preferred group of salt-forming cations represented by $X^+$ is an ion selected from the group consisting of: sodium, potassium, calcium, and magnesium.

More preferably $X^+$ represents a member selected from the group consisting of: $Na^+$, $Ca^{+2}$ and $K^+$.

By including a suitable amount of the carbon dioxide producing compound, preferably sodium bicarbonate or sodium carbonate, one or more of the following stabilized structures is formed

I

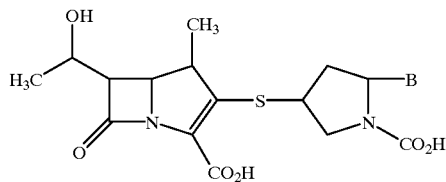

Compound I above, wherein B is described above, is referred to as the free acid form of the stabilized compound. Compounds I-a through I-c are examples of salt forms of the stabilized compound.

I-a

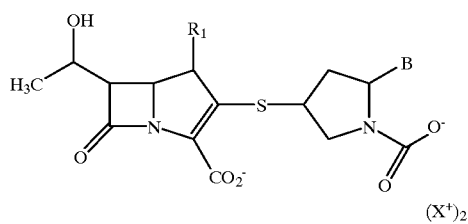

I-b

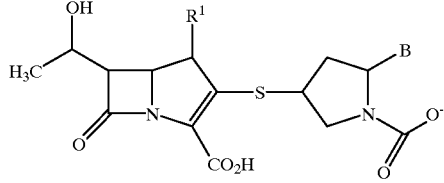

$X^+$

I-c

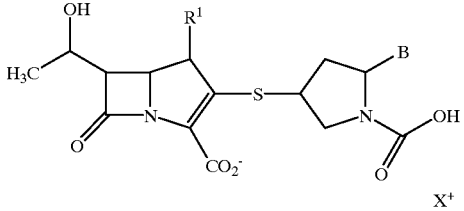

$X^+$ wherein B is:
—$(CH_2)_2S(CH_2)_2C(O)NH_2$, —$(CH_2)_2S(CH_2)_2C(O)NHCH_3$,
—$(CH_2)_2S(CH_2)_2C(O)N(CH_3)_2$, —$(CH_2)_2S(CH_2)_2C(O)N(CH_3)CH_2CH_3$,
—$(CH_2)_2S(CH_2)_2C(O)NHCH_2CN$, —$(CH_2)_2S(CH_2)_2C(O)NH(CH_2)_2OH$,
—$(CH_2)_2S(CH_2)_2C(O)NHCH_2CONH_2$, —$(CH_2)_5C(O)NH_2$,
—$(CH_2)_2S(CH_2)_2C(O)NHCH(OH)CH_2OH$, —$(CH_2)_5C(O)NHCH_3$,
—$(CH_2)_5C(O)N(CH_3)_2$, —$(CH_2)_5C(O)N(CH_3)CH_2CH_3$,
—$C(O)N(CH_3)_2$,
—$(CH_2)_5C(O)NHCH_2CN$, —$(CH_2)_5C(O)NH(CH_2)_2OH$,
—$(CH_2)_5C(O)NHCH_2CONH_2$, —$(CH_2)_5C(O)NHCH(OH)CH_2OH$,
—$CH_2CH(OH)(CH_2)_2NHCH_3$, —$(CH_2)_4NHSO_2CH_3$,

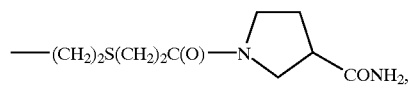

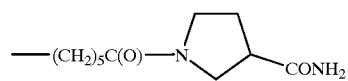

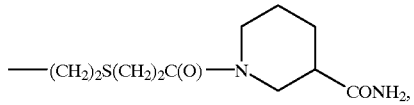

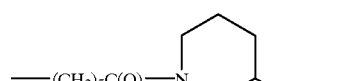

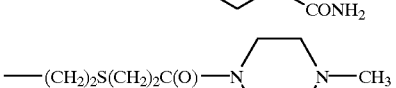

and

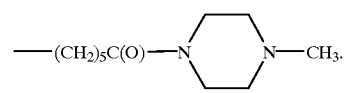

The amount of the carbon dioxide producing compound, e.g., sodium bicarbonate or sodium carbonate which is included in the composition is that which is sufficient to form compounds of formula I through I-c, and which optionally provides the desired pH of the composition upon dissolution or reconstitution.

To provide electronic balance and overall charge neutrality, from zero to three positively charged counterions are present. Different counterions can be included in the composition. Hence, for example, calcium and sodium could be included together in the pharmaceutical composition to provide overall charge neutrality. The counterions can thus be varied within wide limits. Generally the counterion or counterions are pharmaceutically acceptable cationic species.

The carbapenem compound of the present invention is useful for the treatment of bacterial infections in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is concerned with pharmaceutical compositions and methods of treating bacterial infections utilizing the carbapenem compound.

The carbapenem may be used in a variety of pharmaceutical preparations. Compositions for injection, the preferred route of delivery, may be prepared in unit dosage form or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the active ingredient may be in the form of a powder, which can be reconstituted with a liquid such as sterile water, normal saline and the like at the time of administration. The powder can be in lyophilized or non-lyophilized form.

Representative oral compositions are typically in the form of tablets, capsules, solutions or suspensions. Such compositions may likewise be packaged in unit dose or multidose containers. In these oral compositions, the pharmaceutically acceptable carriers may be comprised of diluents, tabletting and granulating aids, lubricants, disintegrants, buffers, sweeteners, preservatives and the like.

Topical compositions may be formulated with pharmaceutically acceptable carriers in the form of hydrophobic or hydrophilic ointments, creams, lotions, solutions, paints or powders.

The dosage to be administered depends to a large extent upon the condition and size of the mammalian patient being treated as well as the delivery route and frequency of administration. The parenteral route (by injection) is preferred.

The compositions for human delivery per unit dosage, whether liquid or solid, may contain from about 0.01% to about 99% of active material, the preferred range being from about 10–60%. The composition will generally contain from about 10 mg to about 3000 mg of the active ingredient; however, in general, it is preferable to employ a dosage amount in the range of from about 100 mg to about 1000 mg. In parenteral administration, the unit dosage is usually the compound in a sterile water or saline solution or in the form of a powder intended for dissolution or reconstitution.

The preferred method of administration of the compound of formula I is parenterally by intravenous (i.v.) infusion. Alternatively, the compound may be administered by injection intramuscularly (i.m.).

For adults, a dose of about 5 to about 50 mg of the formula I antibacterial compound per kg of body weight is administered from 1 to 6 times per day. The preferred dosage ranges from about 100 mg to about 1000 mg of the compound given one to four times per day, preferably 1–2 times a day, and most preferably once daily.

More specifically, for mild infections a dose of about 100 mg to about 1000 mg from one to four times daily is preferred, most preferably once daily. For moderate infections, a dose of about 500 mg to about 1000 mg from one to four times daily is preferred. For severe, life-threatening infections, a dose of about 1000–2000 mg one to six times daily is preferred.

For children, a dose of 5–25 mg/kg of body weight given 1 to 4 times per day is preferred; a dose of 10 mg/kg from one to four times daily is preferred.

The compound of formula I is of the broad class known as carbapenems. Naturally occurring carbapenems are susceptible to attack by a renal enzyme known as dehydropeptidase (DHP). This attack or degradation may reduce the efficacy of the carbapenem antibacterial agent. The compound used in the present invention is significantly less subject to such attack, and therefore may not require the use of a DHP inhibitor. However, use of a DHP inhibitor is optional and is contemplated as being included in the present invention. Inhibitors of DHP and their use with carbapenem antibacterial agents are disclosed in European Patent Applications No. 79102616.4, filed Jul. 24, 1979 (Patent No. 0 007 614); and No. 82107174.3, filed Aug. 9, 1982 ? (Publication No. 0 072 014)].

The compound of the present invention may, where DHP inhibition is desired or necessary, be combined or used with the appropriate DHP inhibitor as described in the aforesaid patents and published application. The cited European Patent Application defines the procedure for determining DHP susceptibility of the present carbapenems and disclose suitable inhibitors, combination compositions and methods of treatment.

A preferred weight ratio of formula I compound: DHP inhibitor in combination compositions is about 1:1. A preferred DHP inhibitor is 7-(L-2-amino-2-carboxyethylthio)-2-(2,2-dimethylcyclopropanecarboxamide)-2-heptenoic acid, or a salt thereof, also known as cilastatin.

The carbapenem is active against various gram-positive and to a lesser extent gram-negative bacteria, and accordingly finds utility in human and veterinary medicine.

The claimed compounds are distinctly stable carbapenem compounds as shown in non-limiting Example 3.

EXAMPLE 3

The plots in FIG. 1 demonstrate the effect of adduct formation on degradation at high drug concentration. Under the conditions (200 mg/mL (4R,5S,6S,8R,2'S,4'S)-3-[[2-[[(3-carboxyphenyl)amino]carbonyl]N-carboxypyrrolidin-4-yl]thio]-4-methyl-6-(1-hydroxyethyl)-7-oxo-1-azabicyclo[3.2.0]hept-2-en-2-carboxylic acid trisodium [compound A]

salt in water) the main route of degradation is formation of dimers. Dimerization in turn is dependent on the presence of the free drug as disodium salt with an unionized pyrrolidine ring nitrogen. Through formation of the stabilized form with $CO_2$, the concentration of free drug sodium salt is decrease. This effect is shown by the plot of % dimers vs. time in the presence of sodium carbonate at pH 7.5 (triangles), where the amount of dimer degradates is controlled to approximately 3% in 8 hours at 5C. Conversely, the plot of % dimers vs. time in the absence of carbonate but at the same pH and temperature (filled circles) shows that dimers grow linearly to over 5% in 6 hours.

Under solid state conditions, stability of the carbonate-buffered Compound A at 25° C. remain constant for twelve or more weeks.

The reaction steps are exemplified by Example 4. The product of the novel process of this invention can be used in the treatment of infectious diseases, including gram positive and negative, aerobic and anaerobic bacteria. The compounds provide good stability against betalactamases, and a favorable duration of action.

EXAMPLE 4

Meropenem (Merrem® 1000 obtained from Zeneca S.P.A., 34.2 mg, equivalent to 25 mg meropenem anhydrous) was placed in a plastic nalgene tube and 1.0 mL of $D_2O$ was added (giving a 25 mg/mL solution). The solution was mixed for several minutes and divided into two parts. The first part was analyzed by proton NMR in a 5 mm tube placed in the magnet of a 200 MHz instrument. The second part (0.5 mL) was diluted with 0.5 mL of a solution of $NaH^{13}CO_3$ (15.8 mg/mL) in $D_2O$, to a total meropenem concentration of 12.5 mg/mL and analyzed by $^{13}C$ NMR in a 5 mm tube in the above mentioned instrument (operating at 50 MHz for carbon). The meropenem adduct with $CO_2$ was observed as a triplet resonance at 4.6 ppm in the proton spectrum (in the upfield slope of the residual water signal) and at 163 ppm in the carbon spectrum (downfield from the bicarbonate signal at 161 ppm).

EXAMPLE 5

Meropenem (340 mg=250 mg anhydrous meropenem) was dissolved in 5 mL USP $H_2O$ (=50 mg/mL meropenem) for approximately five minutes with considerable shaking. The solution was divided into 5×1 mL aliquots in 2 mL lyo-vials and frozen in a lyophilization chamber at −45° C. for 2 hours. The vacuum (ca 50 mtorr) was applied and the following cycle used for drying: ramp at 0.5° C./min to −20° C. and hold 12 hours (primary drying); ramp at 0.5° C./min to +10° C. and hold 12 hours (secondary drying); ramp at 0.5° C./min to +40° C. and hold 24 hours. At the end, the vials were stoppered under vacuum, prior to removal from the lyophilizer. Solid state $^{15}N$ NMR examination revealed approximately 95% of the reconstituted and lyophilized product was present (at about 8.5 ppm) as the carbon dioxide adduct. The solid state 15N NMR experiments were performed on the Bruker DMX-300 NMR spectrometer. The experiments involved magic-angle spinning, cross polarization and proton decoupling. Chemical shifts were reported relative to glycine.

While certain preferred embodiments of the invention have been described herein in detail, numerous alternative embodiments are contemplated as falling within the scope of the appended claims. Consequently the invention is not to be limited thereby.

What is claimed is:
1. A compound represented by the formula I:

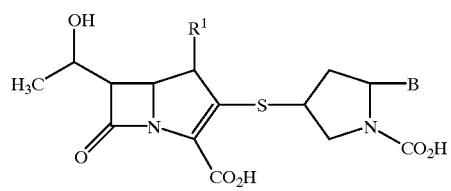

I or a pharmaceutically acceptable salt or hydrate thereof, wherein:

B is selected from a group consisting of H, CN,

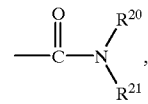

straight or branch chain, $C_{1-6}$ alkyl, $C_{2-6}$ alkenyl, $C_{3-6}$ cycloalkyl and $C_{1-6}$-alkyl-X—$C_{1-6}$ alkyl, wherein X is O, S, NH, or N($C_{1-6}$ alkyl), and wherein said alkyl and alkenyl are optionally substituted with 1 to 3 groups selected from the group consisting of

and $R^2$, wherein X is selected from the group consisting of O and NH, $R^3$ is selected from the group consisting of amino and a heterocyclic group, said amino group can be substituted with

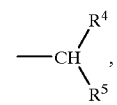

$C_{1-6}$ alkyl, aryl, hydroxy($C_{1-6}$)alkyl, and carbamoyloxy ($C_{1-6}$)alkyl, said heterocyclic group is selected from

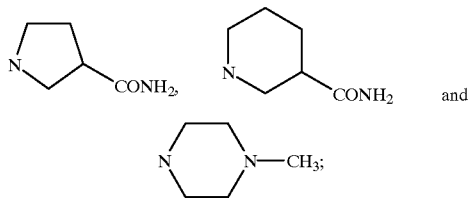

$R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

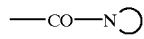

and

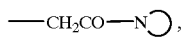

wherein

is a 3 to 6 membered heterocyclic ring which can contain additional hetero atoms, $R^2$ is selected from the group consisting of hydroxy($C_{1-6}$) alkyl, carbamoyloxy, OH, $NR^6SO_2R^6$, and $N(R^6)_2$, $R^6$ is selected from the group consisting of hydrogen and C1–6 alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl, and pyridyl, or $R^{20}$ and $R^{21}$ taken together are selected from the goup consisting of an alkylene chain, and a alkylene chain linked via a $C_2$–$C_3$ alkyl-substituted nitrogen atom to form, together with the adjacent nitrogen atom, a 3 to 7 membered cyclic amino group and $R^1$ is selected from the group consisting of H and $C_{1-6}$ alkyl.

2. A compound according to claim 1 wherein B is selected from a group consisting of

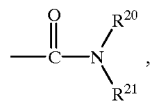

straight or branch chain, $C_{1-6}$ alkyl, $C_{2-6}$ alkenyl, $C_{3-6}$ cycloalkyl or $C_{1-6}$ alkyl-X—$C_{1-6}$ alkyl wherein X is O, S, and NH, wherein said alkyl, and alkenyl is optionally substituted with 1 to 3 groups selected from the group consisting of

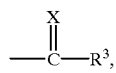

or $R^2$ and X is O.

3. A compound according to claim 1 wherein $R^3$ is

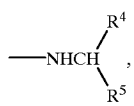

wherein $R^4$ and $R^5$ independently are selected from the group consisting of H, hydroxy($C_{1-4}$)alkyl, CN, carbamoyl ($C_{1-4}$)alkyl, cyano($C_{1-4}$)alkyl, ureido($C_{1-4}$)alkyl, or piperazinyl optionally mono-substituted with carbamoyl, $C_{1-6}$ alkyl, hydroxy($C_{1-4}$)alkyl, CN, carbamoyl($C_{1-4}$)alkyl, cyano($C_{1-4}$) alkyl, ureido($C_{1-4}$)alkyl, amino ($C_{1-4}$)alkyl, carbamoyloxy ($C_{1-4}$)alkyl or mono- or di-($C_{1-4}$)alkyl alkylcarbamoyl($C_{1-4}$) alkyl, and $R^2$ is selected from the goup consisting of hydroxy($C_{1-6}$)alkyl, carbamoylxoy, OH, $NR^6SO_2R^6$, and $N(R^6)_2$.

4. A compound according to claim 1 wherein the pharmaceutically acceptable salt is selected from the group consisting of

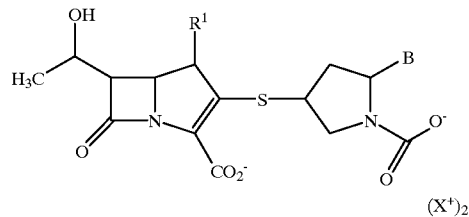

I-a

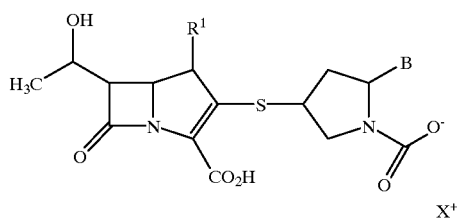

I-b

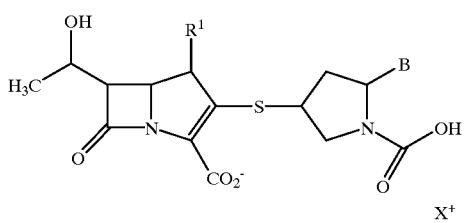

I-c wherein $X^+$ represents a pharmaceutically acceptable cationic group and B is

—$(CH_2)_2S(CH_2)_2C(O)NH_2$, —$(CH_2)_2S(CH_2)_2C(O)NHCH_3$,

—$(CH_2)_2S(CH_2)_2C(O)N(CH_3)_2$, —$(CH_2)_2S(CH_2)_2C(O)N(CH_3)CH_2CH_3$,

—$(CH_2)_2S(CH_2)_2C(O)NHCH_2CN$, —$(CH_2)_2S(CH_2)_2C(O)NH(CH_2)_2OH$,

—$(CH_2)_2S(CH_2)_2C(O)NHCH_2CONH_2$, —$(CH_2)_5C(O)NH_2$,

—$(CH_2)_2S(CH_2)_2C(O)NHCH(OH)CH_2OH$, —$(CH_2)_5C(O)NHCH_3$,

—$(CH_2)_5C(O)N(CH_3)_2$, —$(CH_2)_5C(O)N(CH_3)CH_2CH_3$, —$C(O)N(CH_3)_2$,

—$(CH_2)_5C(O)NHCH_2CN$, —$(CH_2)_5C(O)NH(CH_2)_2OH$,

—$(CH_2)_5C(O)NHCH_2CONH_2$, —$(CH_2)_5C(O)NHCH(OH)CH_2OH$,

—$CH_2CH(OH)(CH_2)_2NHCH_3$, —$(CH_2)_4NHSO_2CH_3$,

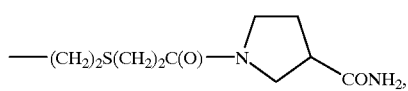

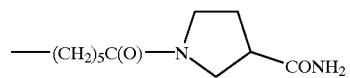

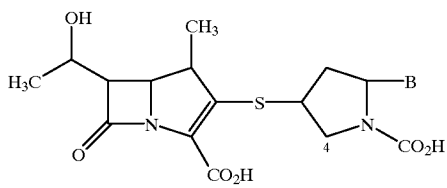

5. The compound of formula I according to claim 1 which is

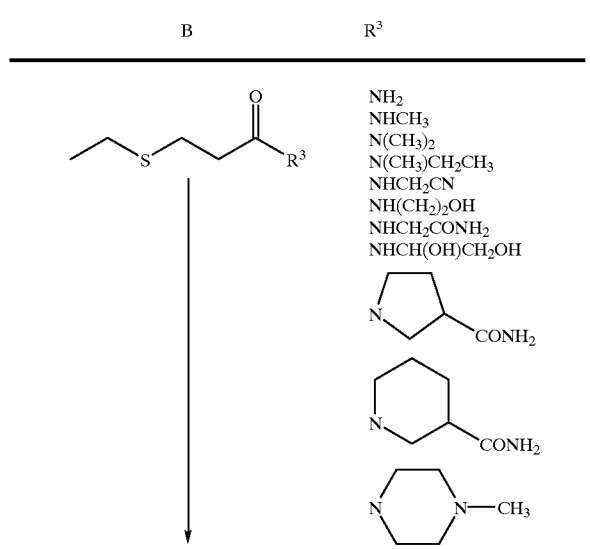

wherein B is selected from the group consisting of:

| B | R³ |
|---|---|
| 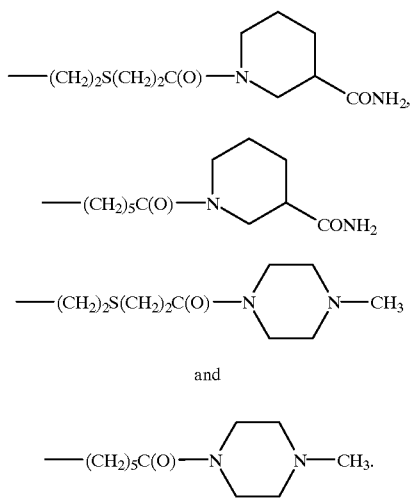 | NH₂<br>NHCH₃<br>N(CH₃)₂<br>N(CH₃)CH₂CH₃<br>NHCH₂CN<br>NH(CH₂)₂OH<br>NHCH₂CONH₂<br>NHCH(OH)CH₂OH |

| B | R³ |
|---|---|
| 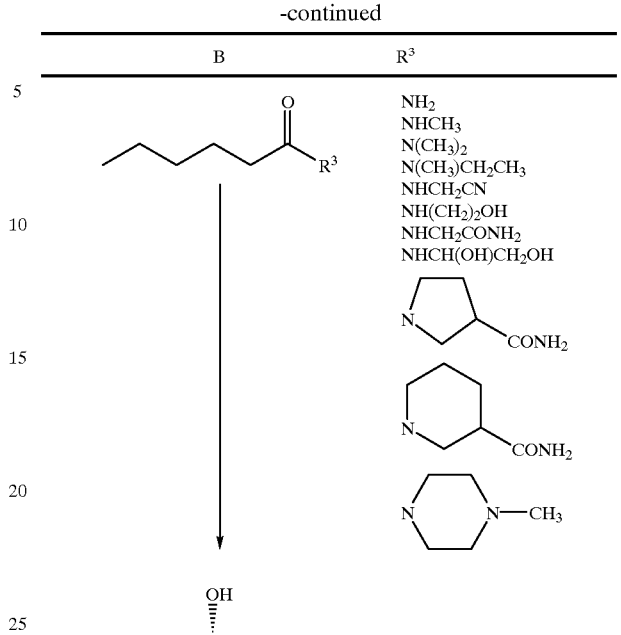 | NH₂<br>NHCH₃<br>N(CH₃)₂<br>N(CH₃)CH₂CH₃<br>NHCH₂CN<br>NH(CH₂)₂OH<br>NHCH₂CONH₂<br>NHCH(OH)CH₂OH |

C(O)N(CH₃)₂, 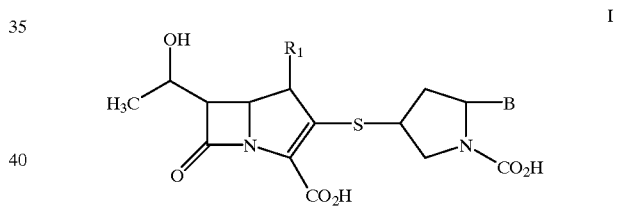 and

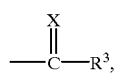

6. A pharmaceutical composition which is comprised of a compound represented by formula I:

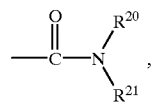

or a pharmaceutically acceptable salt or hydrate thereof, in combination with a pharmaceutically acceptable carrier, wherein:

B is selected from a group consisting of H, CN, $$-\overset{O}{\underset{}{C}}-N\overset{R^{20}}{\underset{R^{21}}{}},$$

straight or branch chain, $C_{1-6}$ alkyl, $C_{2-6}$ alkenyl, $C_{3-6}$ cycloalkyl and $C_{1-6}$-alkyl-X—$C_{1-6}$ alkyl, wherein X is O, S, NH, or N($C_{1-6}$ alkyl), and wherein said alkyl and alkenyl are optionally substituted with 1 to 3 groups selected from the group consisting of $$-\overset{X}{\underset{}{C}}-R^3,$$

and $R^2$, wherein X is selected from the group consisting of O and NH, $R^3$ is selected from the group consisting of amino and a heterocyclic group, wherein the heterocyclic group is selected from the group consisting of

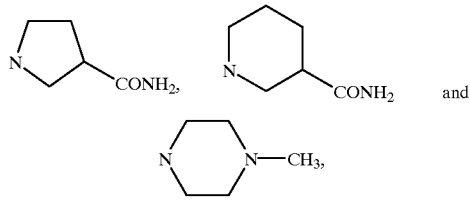

each of which can be substituted with

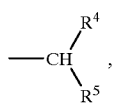

$C_{1-6}$alkyl, aryl, heteroaryl, hydroxy($C_{1-6}$)alkyl and carbamoyloxy($C_{1-6}$)alkyl, said alkyl, aryl, and heteroaryl optionally substituted with 1 to 3 groups selected from H, $COOR^6$, halo, $CF_3$, $C_{1-6}$ alkyl, OH and $N(R^6)_2$, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

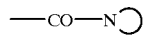

and

wherein

is a 3 to 6 membered heterocyclic ring which can contain additional hetero atoms, $R^2$ is selected from the group consisting of hydroxy($C_{1-6}$) alkyl, carbamoylxoy, OH, $NR^6SO_2R^6$ and $N(R^6)_2$, $R^6$ is selected from the group consisting of hydrogen and $C_{1-6}$ alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl and pyridyl, or $R^{20}$ and $R^{21}$ taken together are selected from the group consisting of an alkylene chain, and a $C_2$–$C_3$ alkyl-substituted nitrogen atom to form, together with the adjacent nitrogen atom, a 3 to 7 membered cyclic amino group guanidyl group of the formula:

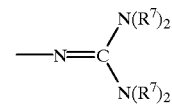

$R^7$ is selected from the group consisting of hydrogen, $C_{1-6}$ alkyl, OH, a $C_{1-6}$ alkoxy, a $C_1$–$C_3$alkyl-hydrazino group, and a group of the formula —$NHOR^8$, wherein $R^8$ is a hydrogen atom, or a $C_{1-6}$ alkyl, and $R^1$ is selected from the group consisting of H and $C_{1-6}$ alkyl.

7. A pharmaceutical composition which is comprised of a compound represented by formula II:

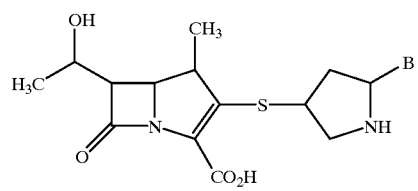

or a pharmaceutically acceptable salt or hydrate thereof, in combination with a carbon dioxide source, wherein:

B is selected from a group consisting of H, CN,

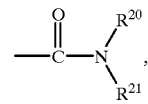

straight or branch chain, $C_{1-6}$ alkyl, $C_{2-6}$ alkenyl, $C_{3-6}$ cycloalkyl and $C_{1-6}$-alkyl-X—$C_{1-6}$ alkyl, wherein X is O, S, NH, or N($C_{1-6}$ alkyl), and wherein said alkyl and alkenyl are optionally substituted with 1 to 3 groups selected from the group consisting of

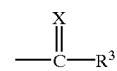

and $R^2$, wherein X is selected from the group consisting of O and NH, $R^3$ is selected from the group consisting of amino and a heterocyclic group, said amino group can be substituted with

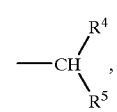

$C_{1-6}$ alkyl, aryl, hydroxy($C_{1-6}$)alkyl, and carbamoyloxy ($C_{1-6}$)alkyl, said alkyl, aryl, and heteroaryl optionally substituted with 1 to 3 groups selected from H, $COOR^6$, halo, $CF_3$, $C_{1-6}$ alkyl, OH and $N(R^6)_2$, said heterocyclic group is selected from

[Structures: pyrrolidine-CONH2, piperidine-CONH2, and N-methylpiperazine]

$R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

—CO—N⟩ and

—CH$_2$CO—N⟩, wherein

—N⟩ is a 3 to 6 membered heterocyclic ring which can contain additional hetero atoms, $R^2$ is selected from the group consisting of bydroxy($C_{1-6}$) alkyl, carbamoyloxy, OH, $NR^6SO_2R^6$ and $N(R^6)_2$, $R^6$ is selected from the group consisting of hydrogen and C1–6 alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl and pyridyl, or $R^{20}$ and $R^{21}$ taken together are selected from the group consisting of an alkylene chain, and a alkylene chain linked via a $C_2$–$C_3$ alkyl-substituted nitrogen atom to form, together with the adjacent nitrogen atom, a 3 to 7 membered cyclic amino group and R1 is selected from the group consisting of H and $C_{1-6}$ alkyl.

8. A pharmaceutical composition in accordance with claim 7 wherein the carbon dioxide source is selected from the group consisting of carbon dioxide, potassium, magnesium, calcium and sodium carbonates/bicarbonates.

9. A pharmaceutical composition in accordance with claim 8 wherein the carbon dioxide source is sodium carbonate or sodium bicarbonate.

10. A pharmaceutical composition in accordance with claim 7 comprising about 3–10 parts by weight of compound II, or a pharmaceutically acceptable salt, stabilized form, prodrug or hydrate thereof, and about 1 part by weight sodium bicarbonate.

11. A pharmaceutical composition in accordance with claim 8 comprising about 3–10 parts by weight of compound II, or a pharmaceutically acceptable salt, stabilized form, prodrug or hydrate thereof, and about 1 part by weight sodium carbonate.

12. A pharmaceutical composition in accordance with claim 7 wherein about 6.7 parts by weight of the compound of formula I, or a pharmaceutically acceptable salt, stabilized form, prodrug or hydrate thereof, are combined with 1 part by weight of sodium carbonate.

13. A pharmaceutical composition in accordance with claim 8 wherein about 6.7 parts by weight of the compound of formula I, or a pharmaceutically acceptable salt, stabilized form, prodrug or hydrate thereof, are combined with 1 part by weight of sodium bicarbonate.

14. A pharmaceutical composition in accordance with claim 7 furffier comprising a dehydropeptidase inhibitor.

15. A pharmaceutical composition in accordance with claim 14 wherein the dehydropeptidase inhibitor is cilastatin.

16. A compound of structural formula I

I

[Structure of formula I: carbapenem with OH, $H_3C$, $R_1$, S-pyrrolidine-B, $CO_2H$, $CO_2H$]

or a pharmaceutically acceptable salt or hydrate thereof, which is produced by reacting a compound of formula II:

II

[Structure of formula II: carbapenem with OH, $H_3C$, $CH_3$, S-pyrrolidine-B (NH), $CO_2H$]

or a pharmaceutically acceptable salt or hydrate thereof with a carbon dioxide source, wherein:

B is selected from a group consisting of H, CN,

[Structure: —C(=O)—N($R^{20}$)($R^{21}$)], straight or branch chain, $C_{1-6}$ alkyl, $C_{2-6}$ alkenyl, $C_{3-6}$ cycloalkyl and $C_{1-6}$-alkyl-X—$C_{1-6}$ alkyl, wherein X is O, S, NH, or N($C_{1-6}$ alkyl), and wherein said alkyl and alkenyl are optionally substituted with 1 to 3 groups selected from the group consisting of

[Structure: —C(=X)—$R^3$]

and $R^2$, wherein X is selected from the group consisting of O and NH, $R^3$ is selected from the group consisting of amino and a heterocyclic group, wherein the heterocyclic group is selected from the group consisting of

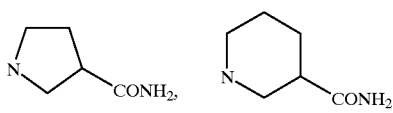

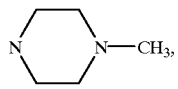

each of which can be substituted with

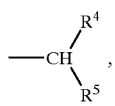

C1–6 alkyl, aryl, heteroaryl, hydroxy($C_{1-6}$)alkyl and carbamoyloxy($C_{1-6}$)alkyl, said alkyl, aryl and heteroaryl optionally substituted with 1 to 3 groups selected from H, $COOR^6$, halo, $CF_3$, $C_{1-6}$ alkyl, OH and $N(R^6)_2$, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)alkyl, mono- or di-($C_{1-6}$)alkylcarbamoyl-($C_{1-6}$)alkyl, ureido ($C_{1-6}$)alkyl,

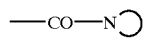

and

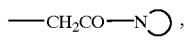

wherein

is a 3 to 6 membered heterocyclic ring which can contain additional hetero atoms, $R^2$ is selected from the group consisting of hydroxy($C_{1-6}$) alkyl, carbamoyloxy, OH, $NR^6SO_2R^6$ and $N(R^6)_2$, $R^6$ is selected from the group consisting of hydrogen and $C_{1-6}$ alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl and pyridyl, or $R^{20}$ and $R^{21}$ taken together are selected from the group consisting of an alkylene chain, and a $C_2$–$C_3$ alkyl-substituted nitrogen atom to form, together with the adjacent nitrogen atom, a 3 to 7 membered cyclic amino group, or a guanidyl group of the formula:

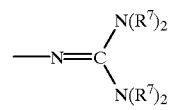

$R^7$ is selected from the group consisting of hydrogen, $C_{1-6}$ alkyl, OH, a $C_{1-6}$ alkoxy, a ($C_1$–$C_3$)alkyl-hydrazino group and a group of the formula —$NHOR^8$, wherein $R^8$ is a hydrogen atom, or a $C_{1-6}$ alkyl, and $R^1$ is selected from the group consisting of H or $C_{1-6}$ alkyl.

17. A compound in accordance with claim 16 wherein the carbon dioxide source is selected from the group consisting of carbon dioxide, potassium, magnesium, calcium, sodium carbonate and sodium bicarbonate.

18. A compound in accordance with claim 17 wherein the carbon dioxide source is selected from the group consisting of sodium carbonate or sodium bicarbonate.

19. A method of stabilizing a carbapenem compound of the formula II:

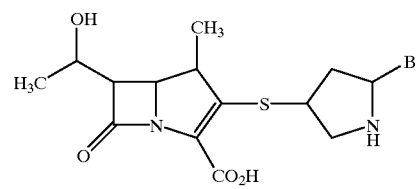

II or a pharmaceutically acceptable salt or hydrate thereof, against degradation >and dimer formation wherein:

B is selected from a group consisting of H, CN,

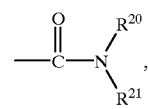

straight or branch chain, $C_{1-6}$ alkyl, $C_{2-6}$ alkenyl, $C_{3-6}$ cycloalkyl and $C_{1-6}$-alkyl-X—$C_{1-6}$ alkyl, wherein X is O, S, NH, or N($C_{1-6}$ alkyl), and wherein said alkyl and alkenyl are optionally substituted with 1 to 3 groups selected from the group consisting of

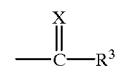

and $R^2$,

Wherein X is selected from the group consisting of O and NH, $R^3$ is selected from the group consisting of amino and heterocyclic group, wherein the heterocyclic group is selected from the group consisting of

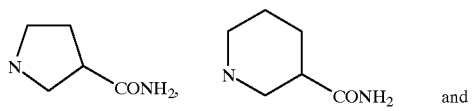

-continued $$\text{N}\diagdown\text{N}-CH_3,$$

each of which can be substituted with a member selected from the group consisting of $$-CH\diagup^{R^4}_{R^5},$$

$C_{1-6}$ alkyl, aryl, heteroaryl, hydroxy($C_{1-6}$)alkyl and carbamoyloxy($C_{1-6}$)alkyl, said alkyl, aryl, and heteroaryl optionally substituted with 1 to 3 groups selected from H, $COOR^6$, halo, $CF_3$, $C_{1-6}$ alkyl, OH and $N(R^6)_2$, $R^4$ and $R^5$ independently are selected from the group consisting of H, hydroxy($C_{1-6}$)alkyl, CN, amino, carbamoyl, carbamoyl($C_{1-6}$)alkyl, cyano($C_{1-6}$)alkyl, mono- or di-($C_{1-6}$)alkylcarbamoyl, carbamoyloxy, ureido, amino($C_{1-6}$)alkyl, carbamoyloxy($C_{1-6}$)akyl, mono- or di-($C_{1-6}$)alkylcarbamoyl-($C_{1-6}$)alkyl, ureido ($C_{1-6}$)alkyl, $$-CO-N\diagup\diagdown$$

and $$-CH_2CO-N\diagup\diagdown,$$

wherein $$-N\diagup\diagdown$$

is a 3 to 6 membered heterocyclic ring which can contain additional hetero atoms, selected from the group consisting of aziridinyl, azetidinyl, pyrrolidinyl, piperidinyl, piperazinyl, and the substitution is selected from the group consisting of carbamoyl, $C_{1-6}$alkyl, hydroxy($C_{1-6}$)alkyl, cyano($C_{1-6}$)alkyl, carbamoyloxy ($C_{1-6}$)alkyl, ureido($C_{1-6}$)alkyl, carbamoyl($C_{1-6}$)alkyl, mono- or di-($C_{1-6}$)alkyl, and carbamoyloxy($C_{1-6}$)alkyl, $R^2$ is selected from the group consisting of hydroxy($C_{1-6}$) alkyl, carbamoyloxy, OH, $NR^6SO_2R^6$, and $N(R^6)_2$, $R^6$ is selected from the group consisting of hydrogen and $C_{1-6}$ alkyl, $R^{20}$ and $R^{21}$ are independently selected from the group consisting of H, $C_{1-5}$ alkyl, $C_{3-5}$ alkenyl, aralkyl group having 1 to 3 carbon atoms in its alkyl moiety, a substituted $C_{1-5}$ alkyl, and pyridyl, or $R^{20}$ and $R^{21}$ taken together are selected from the group consisting of an alkylene chain, and a $C_2$–$C_3$ alkyl-substituted nitrogen atom to form, together with the adjacent nitrogen atom, a 3 to 7 membered cyclic amino group, or a guanidyl group of the formula:

$$-N=C\diagup^{N(R^7)_2}_{N(R^7)_2}$$

$R^7$ is selected from the group consisting of hydrogen, $C_{1-6}$ alkyl, OH, a $C_{1-6}$ alkoxy, a ($C_1$–$C_3$)alkyl-hydrazino group, and a group of the formula —$NHOR^8$, wherein $R^8$ is a hydrogen atom or a $C_{1-6}$ alkyl, comprising: dissolving a compound of formula II and a sufficient amount of a carbon dioxide source in a solvent to form a solution containing a compound of formula I:

I

[Structure of formula I showing a carbapenem with OH, CH₃, H₃C groups, S-linked pyrrolidine with B and CO₂H substituents]

or a pharmaceutically acceptable salt or hydrate thereof, wherein B is described above.

20. A method in accordance with claim 19 wherein the carbon dioxide source is selected from the group consisting of carbon dioxide, potassium, magnesium, calcium, sodium carbonate and sodium bicarbonate.

21. A method in accordance with claim 20 wherein the carbon dioxide source is selected from the group consisting of sodium carbonate and sodium bicarbonate.

22. A method in accordance with claim 19 wherein the solvent is selected from the group consisting of water or saline.

23. A method in accordance with claim 19 wherein the solution is lyophilized to provide a composition containing a compound of formula I, or a salt or hydrate thereof.

* * * * *